United States Patent [19]

Uhing et al.

[11] 4,133,830

[45] Jan. 9, 1979

[54] PROCESS FOR PREPARING ALKYL OR ARYL THIOPHOSPHORUS HALIDES AND MIXED ISOMERS THEREOF

[75] Inventors: Eugene H. Uhing, Pleasantville; Francis A. Via, Yorktown Heights, both of N.Y.

[73] Assignee: Stauffer Chemical Company, Westport, Conn.

[21] Appl. No.: 765,705

[22] Filed: Feb. 4, 1977

[51] Int. Cl.$^2$ .......................... C07H 9/34; C07H 9/42
[52] U.S. Cl. .................................................. 260/543 P
[58] Field of Search .................................... 260/543 P

[56] References Cited

U.S. PATENT DOCUMENTS

| | | | |
|---|---|---|---|
| 3,429,916 | 2/1969 | Baker et al. | 260/543 P |
| 3,726,918 | 4/1973 | Toy et al. | 260/543 P |
| 3,790,629 | 2/1974 | Uhing et al. | 260/543 P |
| 3,803,226 | 4/1974 | Uhing et al. | 260/543 P |
| 3,864,394 | 2/1975 | Ura et al. | 260/543 P |
| 3,879,500 | 4/1975 | Uhing et al. | 260/981 |
| 3,897,491 | 7/1975 | Toy et al. | 260/543 P |
| 3,962,323 | 6/1976 | Toy et al. | 260/543 P |
| 3,968,156 | 7/1976 | Uhing et al. | 260/543 P |
| 3,988,368 | 10/1976 | Ura et al. | 260/543 P |
| 4,000,190 | 12/1976 | Uhing et al. | 260/543 P |
| 4,034,024 | 7/1977 | Toy et al. | 260/543 P |

*Primary Examiner*—Norman Morgenstern
*Attorney, Agent, or Firm*—Paul J. Juettner

[57] ABSTRACT

Improved yields and a lower accumulation of by-product is obtained in the method for preparing compounds of the formula:

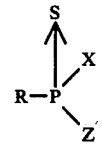

wherein R is a $C_1$ to $C_{20}$ alkyl radical, cycloalkyl of 5-6 carbon atoms in the ring and the $C_1$-$C_4$ alkyl substituted derivative thereof, an aralkyl radical of up to two fused rings, the alkyl portion having from 1 to 20 carbon atoms, an aryl radical of up to three fused rings and the $C_1$-$C_4$ alkyl derivatives thereof, and biphenyl and the $C_1$-$C_4$ alkyl derivatives thereof, X is a halogen of chlorine or bromine, and Z is either R or X, by the reaction of a phosphorus halide source, a hydrocarbon source selected from the group consisting of RH, RX and $RS_aR$, wherein a is 1 or 2 and a sulfur source under autogenous pressure in an autoclave at a temperature ranging from about 175° C. to about 450° C. by recycling to successive runs a by-product of the reaction remaining after separation of the RP(S)XZ product fraction selected from the group consisting of:
(a) a by-product fraction having a boiling point lower than the product fraction;
(b) a by-product fraction having a boiling point higher than the product fraction;
(c) a by-product fraction having a boiling point higher than the product RP(S)XZ wherein Z is R fraction;
(d) XZP(S)RP(S)XZ
(e) liquid residue;
(f) solid residue;
(g) mixtures thereof; and
(h) mixtures of the preceding with $R_2P(S)X$ wherein R and X are as defined hereinbefore.

15 Claims, No Drawings

PROCESS FOR PREPARING ALKYL OR ARYL THIOPHOSPHORUS HALIDES AND MIXED ISOMERS THEREOF

BACKGROUND OF THE INVENTION

Field of the Invention

The present invention relates to new and improved processes for the preparation of alkyl or aryl phosphonothioic dihalides, and phosphinothioic monohalides.

The Prior Art

Alkyl phosphonothioic dihalides have been prepared in the prior art by reacting alkyl halides with phosphorous trihalides in the presence of aluminum chloride, followed by sulfurization of the reaction product. The alkyl halide/phosphorus trihalide reaction proceeds at room temperature according to the formula set forth in Heuben-Weyl, *Methoden der Organis Chenchemie* at Volume 12, Part 1, (1956) at page 396:

$$XR-Cl + PCl_3 + AlCl_3 \rightarrow XR - PCl_4 \cdot AlCl_3 \qquad I.$$

The Heuben-Weyl reference also notes that the reaction has been attempted in the absence of the aluminum chloride catalyst with little success. The reaction has the disadvantage that one mole of aluminum chloride is lost for each mole of product prepared.

More recently, the prior art has taught that alkyl or aryl thiophosphorus halides can be prepared by an autoclave process at 200° C. to 450° C. under at least autogenous pressure. Various reactants can be used as outlined in the following reaction sequences:

| | |
|---|---|
| $RH + P(S)X_3 \rightarrow RP(S)X_2 + HCl$ | (U.S. Pat. 3,790,629) |
| $3RX + 3ZP(S)X_2 + 2P \rightarrow 3RP(S)XZ + 2PX_3$ | (U.S. Pat. 3,726,918) |
| $RSaR + PX_3 + (\text{Sulfur Source})_{2-a} + P \rightarrow RP(S)X_2$ | |
| $a = 1$, U.S. Ser. No. 551,805 | $a = 2$, U.S. Ser. No. 548,650 |
| Filed: 2/20/75, Toy Uhing | Filed: 2/10/75, Toy and Uhing |
| $RX + P(S)X_3 + S \rightarrow RP(S)X_2 + SX_2$ | (U.S. Pat. 3,726,918) |

The thiophosphoryl halide used in these reactions can be prepared in situ by the reaction of phosphorus trichloride and sulfur from a source of available sulfur. The disclosures of the above noted patents and applications are incorporated herewith by reference.

Each of these reactions is plagued by low yields, and by-product formation. For instance, the $RH/P(S)X_3$ reaction disclosed in U.S. Pat. No. 3,790,629 can be operated successfully on a laboratory scale but the laboratory process cannot be economically scaled up to plant scale. In the laboratory, the reaction was conducted with large excesses (150%) of hydrocarbon (See Example 1 of U.S. Pat. No. 3,790,629). A yield of $RP(S)X_2$ of 70% was obtained. It is indicated that further increases could be obtained by recycling by-product $R_2P(S)X$. Since the price of the hydrocarbon has risen significantly and since government regulations may not allow venting the excess hydrocarbon into the air, any manufacturing operation must include a reclamation or disposal stage for the hydrocarbon. Reclamation of the hydrocarbon would require the removal of entrained HX by-product from the hydrocarbon waste stream. Disposal would involve burning a reactant whose price is significant to the economic viability of the process.

An attempt to reduce the quantity of hydrocarbon used in the reaction was unsuccessful. Yields were lowered substantially and a large quantity of by-product residue including solid residues was obtained.

A portion of the problem can be overcome by recycling the by-product $R_2P(S)X$ as taught in U.S. Pat. No. 3,790,629. However, this requires a further distillation step beyond product separation. The problem of solid and liquid residues as well as low yields would not be overcome.

Similarly, in the other named reactions, yields as well as by-products accumulation can be a problem.

It has now been found that yields in these reactions can be easily increased without extensive processing changes. In most instances, by-product accumulation is reduced or in some cases essentially ceases.

THE INVENTION

In accordance with the present invention, it has now been found that the yield of product can be increased and the cumulative yield of by-product can be decreased in the autoclave process for preparing compounds of the formula:

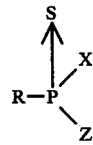

wherein R is a $C_1$ to $C_{20}$ alkyl radical, cycloalkyl of 5-6 carbon atoms in the ring and the $C_1$-$C_4$ alkyl substituted derivative thereof, an aralkyl radical of up to two fused rings. The alkyl portion having from 1 to 20 carbon atoms, an aryl radical of up to three fused rings and the $C_1$-$C_4$ alkyl derivatives thereof, and biphenyl and the $C_1$-$C_4$ alkyl derivatives thereof, X is a halogen of chlorine or bromine, and Z is either R or X, by the reaction of a phosphorus halide source, a hydrocarbon source selected from the group consisting of RH, RX, and RSaR wherein a is 1 or 2 and a sulfur source under autogenous pressure in an autoclave at a temperature ranging from about 175° C. to about 450° C. by recycling in successive runs a byproduct of the reaction remaining after separation of the RP(S)XZ product fraction selected from the group consisting of:

(a) a by-product fraction having a boiling point lower than the product fraction;

(b) a by-product fraction having a boiling point higher than the production fraction;

(c) a by-product fraction having a boiling point higher than the product RP(S)XZ wherein Z is R fraction;

(d) XZP(S)RP(S)XZ;

(e) liquid residue;

(f) solid residue;

(g) mixtures thereof; and (h) mixtures of any of the preceding with $R_2P(S)X$ wherein R and X are as defined hereinbefore.

It has suprisingly been found that recycling some and preferably all of the by-products of the reaction including solid residues will result in increased yields. In connection with the reaction between a hydrocarbon and P(S)Cl$_3$, yields as high as 92% have been obtained using substantially stoichiometric quantities of hydrocarbon. It has also been surprisingly found in connection with the hydrocarbon reaction that residue accumulation in the reaction eventually becomes static with no further buildup when the liquid and solid by-products are continuously recycled to successive runs. This eliminates the need to clean the autoclave between runs. Also, the amount of waste is decreased reducing handling and disposal problems. Waste elimination as an ongoing requirement between runs is no longer necessary. The use of substantially stoichiometric quantities of hydrocarbon eliminate the need for extensive recovery disposal systems for excess hydrocarbon. A conservation of raw materials is achieved as less starting material goes into by-product waste.

In other reactions, yields are also increased but the by-product continues to accumulate though to a lesser degree. While the distillation by-products remaining after product removal appear to cease to accumulate, the solid residues in the autoclave accumulate contributing to an increase in the overall by-product accumulation.

The preferred phosphorus reactant is the chloro compound. The preferred hydrocarbon source is an aliphatic hydrocarbon. The preferred system uses thiophosphoryl chloride. Some of the dihalide products are known and have utility as chemical intermediates - particularly in the preparation of insecticides, fungicides, pharmaceuticals, and other organophosphorus compounds.

DETAILED DESCRIPTION OF THE PRESENT INVENTION

Compounds of the formula: R-P(S)XZ can be readily formed by the following illustrative reactions:

| | |
|---|---|
| RH + P(S)X$_3$→RP(S)X$_2$ + HCl | (U.S. Pat. 3,790,629) |
| 3RX + 3ZP(S)X$_2$ + 2P→3RP(S)XZ + 2PX$_3$ | (U.S. Pat. 3,726,918) |
| RSaR + PX$_3$ + (Sulfur Source)$_{2-a}$ + P→RP(S)X$_2$ | |
| a = 1, U.S. Ser. No. 551,805 | a = 2, U.S. Ser. No. 548,650 |
| Filed: 2/20/75, Toy Uhing | Filed: 2/10/75, Toy and Uhing |
| RX + P(S)X$_3$ + S→RP(S)X$_2$ + SX$_2$ | (U.S. Pat. 3,726,918) |

The thiophosphoryl halide used in these reactions can be prepared in situ by the reaction of phosphorus trihalide and sulfur from a source of available sulfur. The disclosures of the above noted patents and applications is incorporated herewith by reference. All of these reactions utilize a hydrocarbon source (RH, RX, RSR or RSSR), a phosphorus halide source (PX$_3$, P(S)X$_3$, ZP(S)X$_2$) and a sulfur source (ZP(S)X$_2$, P(S)X$_2$, S, RSR, RSSR, P$_4$Sx wherein x is 3 to 10). The reactions using an RX compound as a starting material generally include a halogen acceptor such as phosphorus or sulfur. Any one compound can satisfy more than one source requirement as long as the compound acts as the source for the desired material. As illustrative, thiophosphoryl chloride, P(S)Cl$_3$, can act as both the phosphorus halide source and as the sulfur source. Similarly, thioethers and polysulfides RSaR can act as source for both sulfur and the hydrocarbon. When a equals 1, an additional sulfur source such as sulfur or one or more phosphorus sulfides is generally included. Source compounds formed in situ are intended to be included within the definition of the source of the desired material.

As used in the formulae herein, X is halogen of chlorine or bromine, preferably chlorine. For most intermediate type reactions, chlorine is preferred. Bromine, though more expensive than chlorine, can be used with equal facility if desired. If two or more halogens are present, a mixture of halogens can be used though it is preferred that the halogen be of the same element.

As used in the formulae herein, R can be a C$_1$ to C$_{20}$ alkyl group and preferably the C$_1$ to C$_6$ alkyl group. The R group is also intended to include the aryl substituted derivatives (1 or 2 fused rings) of the alkyl groups, i.e., aralkyl, or any other modifications of the alkyl radicals with noninterfering substituents. The alkyl groups are represented by methyl, ethyl, n-propyl, and isopropyl, n-butyl, isobutyl, and tert-butyl, as well as pentyl, hexyl, heptyl, octyl, nonyl, decyl, dodecyl, tetradecyl, hexadecyl, octodecyl, and eicosyl. The aralkyl groups are represented by phenylmethyl, phenylethyl, phenylbutyl, phenyloctyl, phenylhexadecyl, and the corresponding naphthyl derivatives.

R can also be cycloalkyl or 5-6 carbons in the ring and the C$_1$-C$_4$ alkyl substituted derivatives thereof. These ring systems are illustrated by cyclopentyl and cyclohexyl and its derivatives.

R can also be an aryl of up to and including 3 fused rings. These aromatic compounds include the benzene series, the naphthalene series and the anthracene series of ring compounds and preferably those of the benzene series. Included within each series are those compounds wherein the ring hydrogens are substituted with noninterfering groups. Some of these non-interfering groups can be illustrated by the C$_1$ to C$_4$ alkyl derivatives (alkaryl) which are given only as illustrative of the many equivalent groups which could be used by one skilled in the art. These aryl radicals can be illustrated by phenyl, methylphenyl, i.e., (tolyl), ethylphenyl, propylphenyl, and butylphenyl, naphthyl, methylnaphthyl, ethylnaphthyl, propylnaphthyl, butylnaphthyl, anthryl, methylanthryl, propylanthryl, butylanthryl, as well as mixed forms thereof such as dimethylphenyl, dimethylnaphthyl, diethylanthryl, and the like.

Any of these radicals can contain one or more alkyl radicals. Any isomeric form of these radicals can be used.

The R group can also be biphenyl. Also included in the term biphenyl are the C$_1$ to C$_4$ derivatives such as methylbiphenyl and ditolyl. The substituents can be one or more in any isomeric position desired. The phosphorus in the final product can be attached o, m or p to the biphenyl linkage.

Representative hydrocarbons which can be used in the present invention include methane, ethane, propane, butane, pentane, hexane, octane, dodecane, hexadecane, eicosane, cyclopentane, cyclohexane, benzene, naphthalene, anthracene, toluene, xylene, ethylbenzene, propylbenzene, butylbenzene, biphenyl, and the like. Isomeric forms of the same compound are also included.

Representative alkyl or aryl halide which can be used in the present invention include methyl chloride, ethyl chloride, propyl chloride, butyl chloride, hexyl chloride, octyl chloride, decyl chloride, dodecyl, chloride, hexadecyl chloride, octydecyl chloride, eicosyl chloride, and the corresponding bromo substituted derivatives; and chlorobenzene, bromobenzene, chlorotoluene, chloroethyl benzene, bromoethyl benzene, chloropropyl benzene, bromopropyl benzene, chlorobutyl benzene, bromobutyl benzene, chloromethyl naphthalene, bromomethyl naphthalene, chloroethyl naphthalene, bromoethyl naphthalene, chloropropyl naphthalene, bromobutyl naphthalene. Isomeric forms of the same compound are also included. The foregoing compounds are given as illustrative and are in no way considered to be totally inclusive of all of the alkyl and aryl halides which can be used in the method of the present invention.

Representative dialkyl and diaryl thioethers within the formula RSaR wherein a is 1 include dimethyl, dipropyl, dibutyl, dioctyl, didecyl, didodecyl, dihexadecyl, dioctadecyl, dieicosyl, dicyclopentyl, dicyclohexyl, dibenzyl, ditolyl, diethylbenzyl, dipropylbenzyl, dibutylbenzyl, dinaphthyl, dimethylnaphthyl, dibutylnaphthyl, dianthryl, dimethylanthryl, and dibutylanthryl thioethers, mixed isomers thereof and the like.

Representative compounds within the formula RSaR wherein a is 2 include dimethyl disulfide, dipropyl disulfide, dibutyl disulfide, dioctyl disulfide, didecyl disulfide, didodecyl disulfide, dihexadecyl disulfide, dioctadecyl disulfide, dieicosyl disulfide, dicyclopentyl disulfide, dicyclohexyl disulfide, dibenzyl disulfide, ditolyl disulfide, dibutylbenzyl disulfide, dinaphthyl disulfide, dimethylnaphthyl disulfide, diethylnaphthyl disulfide, dimethylanthryl disulfide, dibutylanthryl disulfide and the like.

The foreoing compounds are given as illustrative and are in no way considered to be totally inclusive of all of the dialkyl and diaryl disulfides which can be used in the method of the present invention. Preparation of such disulfides is described in *Synthetic Organic Chemistry* by R. B. Wagner and H. D. Zook (Wiley, 1953) at Chapter 33.

The phosphorus halide source includes the compounds of the formulae: $PX_3$, $P(S)X_3$ as well as $ZP(S)X_2$, wherein X is halogen, and Z is R or, preferably, X. While Z can be the same as R forming the compound $R_2P(S)X$, the degree of replacement is not as complete and relatively lower yields are obtained. When Z is X, the phosphonothioic halide is formed. When Z is R, the phosphinothioic monohalide is formed. Illustrative sources of the phosphorus halide include phosphorus trichloride, phosphorus tribromide, thiophosphoryl chloride, thiophosphoryl bromide, mixed phosphorus halides such as dichlorothiophosphoryl bromide and dibromothiophosphoryl chloride, methylphosphonothioic dichloride, ethylphosphonothioic dichloride, isopropylphosphonothioic dichloride, benzylphosphonothioic dichloride, phenylphosphonothioic dichloride, cyclohexylphosphonothioic dichloride, decylphosphonothioic dichloride, hexadecylphosphonothioic dichloride, eicosylphosphonothioic dichloride, naphthylphosphonothioic dichloride, anthracylphosphonothioic dichloride, biphenylylphosphonothioic dichloride, tolylphosphonothioic dichloride, and the like. Also, the thio reactants can be made in situ using the corresponding trivalent phosphorus compound and sulfur. Thus, thiophosphoryl chloride can be prepared in situ from phosphorus trichloride and sulfur. This reaction is preferably catalyzed with known catalysts therefor such as carbon. The corresponding alternatives for the other thio reactants would be apparent to one skilled in the art. In the reactions using RX as a reactant and phosphorus as the halogen acceptor, the by-product phosphorus trihalide can be considered a partial phosphorus halide source. For economical reasons, the phosphorus halide is preferably thiophosphoryl chloride. Mixtures of pentavalent thiophosphorus halides can be used without departing from the scope of the invention.

The sulfur source can be derived from sulfur itself, as well as other inorganic and organic sulfides. Organic sulfides such as RSaR which have been discussed hereinbefore can be used as both the hydrocarbon and the sulfur source. Also inorganic sulfides such as the phosphorus sulfides can be effectively used. These are illustrated by $P_4S_3$, $P_4S_5$, $P_4S_7$ and $P_4S_{10}$. These materials provide not only sulfur but also phosphorus for the reaction. A portion of the sulfur source can be derived by the autoclave residues since some of the solid by-products of the reaction are phosphorus sulfides. Other inorganic sources include thiophosphoryl chloride and bromide. These are preferred since they provide a source for both the phosphorus halide and the sulfur while being relatively inexpensive. Any compound which can provide the needed sulfur for the reaction without inducing undesirable side reactions can be used as the sulfur source.

The stoichiometry of the reactions is set forth in the pertinent patents relative thereto. As illustrative, the reaction between an RH compound and a $ZP(S)X_2$ compound appears to require a ratio of 1 mole of the hydrocarbon (RH) and 1 mole of the $ZP(S)X_2$ compound to prepare one mole of the product and one mole of HX by-product. While the stoichiometry appears to dictate a molar ratio of 1 mole hydrocarbon source to 1 mole thiophosphorus compound, an excess of either reactant can be used. If it is desired to conduct the reaction in the presence of a diluent, excess hydrocarbon can act as the diluent. The reaction between the RX compound and $P(S)X_3$ requires 3 moles of RX to 3 moles of $P(S)X_3$ to 2 moles of phosphorus (halogen acceptor) to yield 3 moles of $RP(S)X_2$ and 2 moles of $PX_3$. Excesses of either reactant are generally not desirable as these excesses tend to cause the formation of undesirable by-products.

It is to be pointed out that use of large excesses of hydrocarbon in the $RH/ZP(S)X_2$ reaction, such as ethane and thiophosphoryl chloride, reduce the solid residues in the reaction significantly. However, the excess hydrocarbon cannot be easily recycled as it becomes mixed with the HX by-product requiring extensive purification systems. When the hydrocarbon is reduced to near stoichiometric quantity, solids buildup occurs. The recycling of the present invention allows for the use of near stoichiometric quantities of hydrocarbon while increasing overall product yield.

In all reactions, variations can be made in reactants to lessen any problem of residue buildup. Thus, excess $PX_3$ could be added to withdraw some of the sulfur from the phosphorus sulfides in the solid residue. Any buildup in $PX_3$ can be lessened by adding excess sulfur and reducing the phosphorus halide in the charge. These variations would be of assistance in controlling the residue formation in the reactions other than the $RH/ZP(S)X_2$ reaction since these other reactions accumulating residue particularly the autoclave residue.

The process of the present invention is carried out at elevated temperature and at least at autogenous pressure. Temperatures of between about 175° C. and about 450° C. can be used though temperatures of 200° C. to 400° C. are generally employed. Optimum reaction temperature is related to the reactivity of the hydrocarbon or the halide thereof and the residence time of the reaction. It has been found that methane requires more heat to effect reaction than ethane. Similarly, it has been found that propane requires less heat to effect reaction than ethane and the reaction appears to proceed through the hydrogen of the $CH_2$ group, i.e., a secondary hydrogen with a kinetic preference to the primary H of the $CH_3$ group. Reaction of tertiary butane requires less heat than propane and the reaction proceeds through the tertiary hydrogen. Thus, any hydrocarbon compound which has a tertiary hydrogen atom apparently tend to react principally through the tertiary hydrogen. If the temperature of reaction is high enough, the secondary hydrogen apparently will also react. Similarly, if a high enough temperature is used, the primary hydrogen apparently will also react. Thus, selection of temperature can be guided by the type of compound desired. Aryl hydrogens are generally equivalent in reactivity. Alkyl substituted aryl groups can be affected by temperature since hydrogens on the aryl ring and the alkyl group are reactive sites. These are general guidelines given to assist in practicing the invention and applications do not intend to be limited thereby. The basis for the assumption that the reactions are proceeding through any specific hydrogen atom is theoretical and applicants do not intend to be limited by such statements.

The method of the present invention may conveniently be effected by introducing the individual reactants into a reaction zone capable of withstanding elevated pressure, such as a metal bomb, autoclave, or other pressure vessel, and carrying out the reaction under at least the autogenous pressure developed by the reactants at the reaction temperature. If the reactants are corrosive, a glass lined autoclave could be used. Pressures of up to 200 atmospheres above the autogenous pressure can also be used but are less desirable due to the inconvenience of requiring a pressurization system. The time of reaction may vary over relatively wide limits such as between about 1 to 30 hours, but the preferable reaction time has been found to be between about 2 to 20 hours.

In general, the reaction vessel should be equipped with an agitation mechanism such as a rocker, vibrator, or stirrer assisted by internal baffles for best results. If the thiophosphoryl halide is used, care is to be taken to avoid the presence of water in the system as the compound is hydrolyzed by water.

The reaction may be carried out in continuous or batchwise systems as desired.

In the batch system, the reactor, after an initial run, is charged with fresh reactant and any by-product which has been separated from a preceding run. It is not necessary that the recycle be from the next preceding run as it might be desirable to recharge the reactor and run a reaction while the product and by-products are being separated or use by-products from another reactor. It is also not necessary to clean the reactor prior to the next run. It is desirable that all solid residue be recycled to prevent further buildup. The residue, which contains phosphorus sulfides, also acts as a possible phosphorus and sulfur source in the reaction. However, the solid residue cannot remain in the autoclave indefinitely. Charring and other degradiation reactions will eventually require removal of some of the solid residue. A series of twenty or more runs could be made without difficulty. Liquid residues can be easily recycled by washing them into the reactor with a portion of the fresh charge. It is not necessary that all liquid or solid by-products be recycled but it is preferred practice to recycle all by-products to reduce the overall by-product accumulation. In a continuous system, the by-products can be recycled along with the charge.

The reaction may also be conducted in the presence of diluents which can be gaseous, liquid, or solid at room temperature though this is less desirable. The reaction temperature and time are important variables and should be closely controlled as poly-substitutions are possible. Also, the pentavalent phosphonic or thiophosphoryl halide, $ZP(S)X_2$ can often be present in excess to act as a diluent.

The products of the reaction are purified by conventional methods such as by fractional distillation of liquids and extraction of solid products. However, since all by-products can be recycled, it is only necessary to isolate the product fraction. This is generally accomplished by separating the low boiling fraction by vacuum followed by a heated vacuum distillation to isolate the product. The distillation bottoms which contain $R_2P(S)X$ can be redistilled to separate the $R_2P(S)X$ compounds. The entire bottoms from either distillation can be recycled to the reaction vessel. Since the by-product material can be recycled, it is preferable that the handling steps be limited to avoid material loss. The identification or products is achieved by conventional methods, such as elemental analysis, gas chromatography for purity, and mass spectrometer, $^{31}P$ and $^1H$ nuclear magnetic resonance NMR and infrared analysis to establish structure.

Illustrative of the compounds which can be prepared by the method of the present invention are:

Alkyl $CH_3P(S)Cl_2$
$C_2H_5P(S)Cl_2$
$C_3H_7P(S)Cl_2$
$C_4H_9P(S)Cl_2$
$C_5H_{11}P(S)Cl_2$
$C_8H_{17}P(S)Cl_2$
$C_{18}H_{37}P(S)Cl_2$
$(CH_3)_3C-CH_2P(S)Cl_2$
$CH_3(CH_2)_4-CH-(C_2H_5)CH_2P(S)Cl_2$

Dialkyl $(CH_3)_2P(S)Cl$
$(C_2H_5)_2P(S)Cl$
$(C_4H_9)_2P(S)Cl$
$(C_8H_{17})_2P(S)Cl$
$(C_{18}H_{37})_2P(S)Cl$ Aralkyl

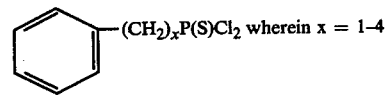
$-(CH_2)_xP(S)Cl_2$ wherein x = 1-4

Crylic
Compounds
Aromatic Series
Benzene Series

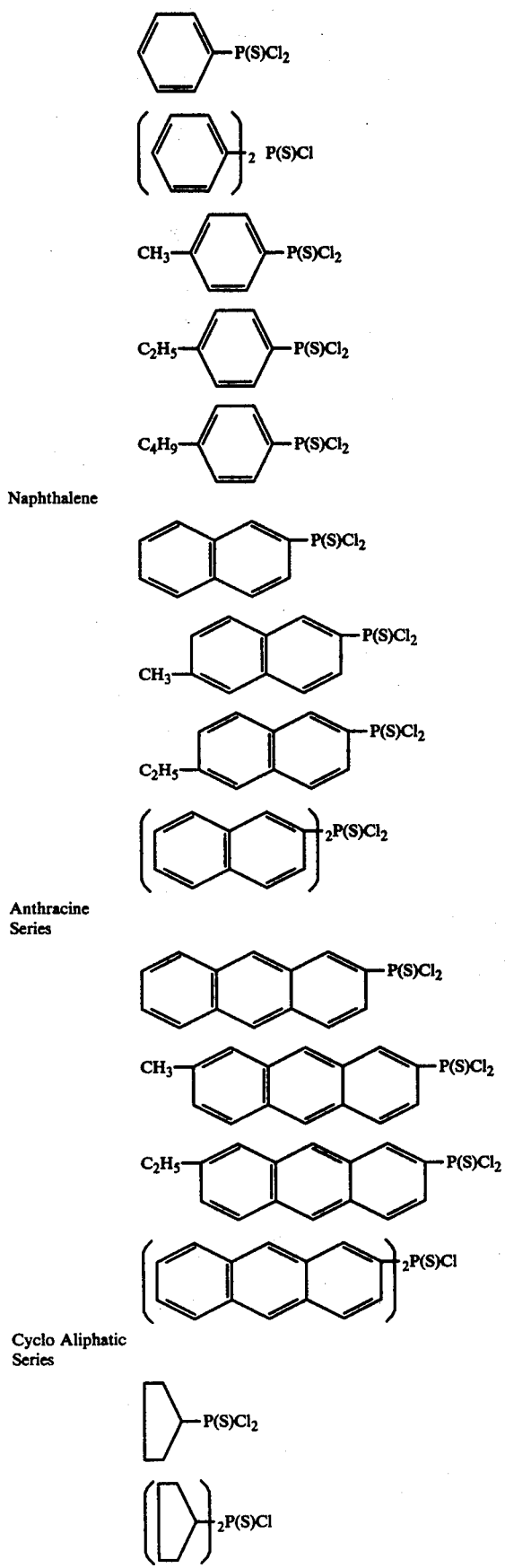

Naphthalene

Anthracine Series

Cyclo Aliphatic Series

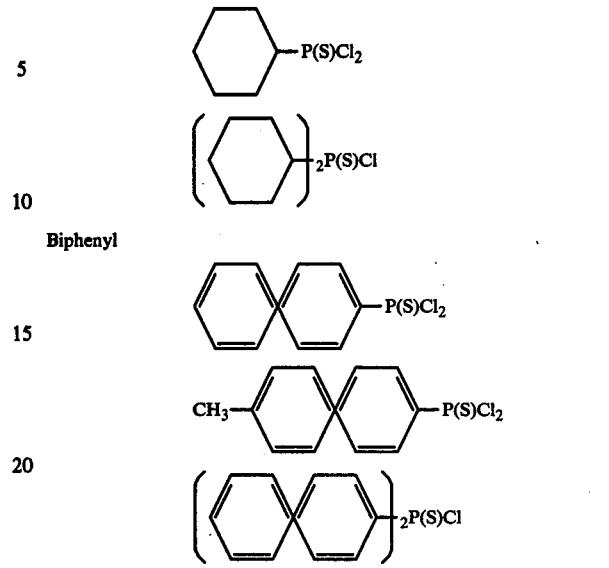

Biphenyl

It is to be pointed out that mixtures of product may be prepared using the alkaryl or aralkyl reactants as these materials contain reactive cites on both the aromatic ring and on the aliphatic chain. The product mixture may contain some alkaryl product as well as some aralkyl product. The amount of each in the mixture depends on the conditions of reaction and the relative reactivity of the alkyl moiety vis-a-vis the aryl moiety.

The products of the present invention are monohalides or dihalides of pentavalent thiophosphorus and, therefore, can be subject to all the known reactions which such compounds undergo. The compounds of the invention can be used as intermediates to make insecticides as illustrated by the process for making O-ethyl S-phenyl ethylphosphonothioate as per the following illustrative reaction scheme:

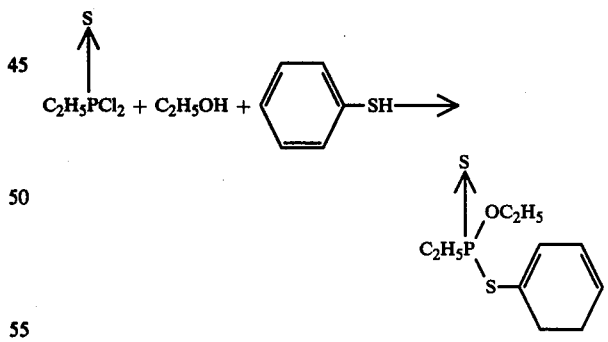

The sodium salts of the acids can also be prepared. Other uses would be obvious to one skilled in the art.

The present invention will be more fully illustrated in the examples which follow:

EXAMPLES 1–14

Preparation of Ethyl Phosphonothioic Dichloride

In a 300 milliliter 316 stainless steel autoclave equipped with a thermocouple well, a pressure blow-out disc rated at 5000 psi and a rocking type agitator were placed 100 grams P(S)Cl$_3$ (0.59 moles). The autoclave was flushed with nitrogen, sealed and fitted with an inlet value and blow-out assembly. The autoclave was cooled in liquid nitrogen and evacuated to 10-15 mm Hg with a water aspirator. 22.2 grams of ethane (0.74 mole) representing a 0.15 mole or 25% excess over the theoretical 0.59 mole based on the amount of PSCl$_3$ used was distilled into a liquid nitrogen trap and the trap was weighed. The ethane was then distilled into the autoclave and the autoclave valve was closed. The autoclave was weighed and placed in a rocking heated jacket. The autoclave was heated according to the following schedule:

TABLE I

| Time (hours) | Temperature (° C) |
|---|---|
| 1.0 | Warm to 300° |
| 0.5 | Heat from 300° to 340° |
| 3.6 | Run between 335°-345° |
| 0.25 | Cool from 340° to 300° |
| 1.5 | Cool from 300° to 120° |
| 1.5 | Cool from 120° to 50° |

The autoclave was cooled by air circulation. After weighing the autoclave and observing no weight loss, the gaseous ingredients were slowly vented into an aqueous scrubber which was connected to a wet test meter. The amount of by-product HCl was determined by neutralizing the scrubbing water with NaOH. The amount of unreacted ethane was recorded by the wet test meter. After venting, the autoclave was opened and the liquid product was poured out. The autoclave was flushed with nitrogen and sealed without cleaning.

The crude product was charged into a distillation flask equipped with a cold finger condenser, packed with perforated stainless steel rectangles a collecting flask and a dry-ice trap. A vacuum (15 mm Hg) was applied to the flask at room temperature (20°-25° C.). Any dissolved HCl was permitted to escape. The collecting flask was cooled in ice water to prevent loss of any PCl$_3$ by evaporation.

The distillation flask was then heated (flask - 85° C., head-67° C.) under the vacuum of 15 mm. Hg. The total weight collected in the collection flask to this point was determined and labelled fraction one.

The material in the distillation flask was then distilled at a temperature of 120° C. (flask) and 108° C. (head) under the 15 mm Hg vacuum. This fraction labelled the second or product fraction was collected and weighed. Analysis confirmed the product to be C$_2$H$_5$P(S)Cl$_2$. The physical data of the product corresponded with the known data for C$_2$H$_5$P(S)Cl$_2$.

The weight of the material remaining in the distillation flask (still bottoms) and the trap were also recorded. These materials were then recycled.

The yields are reported in Table II below. The abbreviation EPTD as used in the Table refers to ethyl phosphonothioic dichloride, i.e., the product fraction.

TABLE II

A Fourteen Run Recycle Series for EPTD Synthesis

| Example | Distillation Weight Data Fraction 1 (grams) | Fraction 2 EPTD (grams) | EPTD Yield Accumulation (grams) | EPTD Yield on P(S)Cl$_3$ weight % | Distillation Bottoms (grams) | Autoclave Residuals (grams) | Total[1] Residuals (grams) | Accumulation Re-Cycle Stream[2] (grams) |
|---|---|---|---|---|---|---|---|---|
| 1 | 14.7 | 50.2 | 50.2 | 53.4 | 16.0 | 8.0 | 24.0 | 38.7 |
| 2 | 24.3 | 68.0 | 118.2 | 69.9 | 24.0 | 11.0 | 35.0 | 59.3 |
| 3 | 25.1 | 79.5 | 197.7 | 82.1 | 27.2 | 15.0 | 42.2 | 67.3 |
| 4 | 19.3 | 80.4 | 278.1 | 84.6 | 25.7 | 23.0 | 48.7 | 68.0 |
| 5 | 21.2 | 82.0 | 360.1 | 84.3 | 28.2 | 27.0 | 55.2 | 76.4 |
| 6 | 16.7 | 80.7 | 440.8 | 83.0 | 27.8 | 32.0 | 59.8 | 76.5 |
| 7 | 18.0 | 83.0 | 523.8 | 85.5 | 30.1 | 32.0 | 62.1 | 80.1 |
| 8 | 19.2 | 88.3 | 612.1 | 91.1 | 30.4 | 32.0 | 62.4 | 81.6 |
| 9 | 19.3 | 89.8 | 701.9 | 92.2 | 33.2 | 28.0 | 60.2 | 80.5 |
| 10 | 20.0 | 90.8 | 792.7 | 93.0 | 33.2 | 33.0 | 65.2 | 86.2 |
| 11 | 20.6 | 89.7 | 882.4 | 91.5 | 31.9 | 29.0 | 60.9 | 81.5 |
| 12 | 18.1 | 86.7 | 969.1 | 89.9[3] | 30.5[3] | 30.0 | 60.5 | 78.6 |
| 13 | 15.8 | 86.0 | 1,055.1 | 89.0 | 32.7 | 32.0 | 64.7 | 80.5 |
| 14 | 18.8 | 90.1 | 1,145.2 | 92.0 | 29.6 | 33.0 | 62.6 | 81.4 |

[1]Total Residuals consists of the residuals of the distillation and the autoclave
[2]The recycle stream consists of Fraction 1 and the total residuals.
[3]3-4% loss of crude on venting.

Each fraction and the still bottoms were analyzed by gas chromotography using a Hewlitt-Packard Model 700 gc equipped with a six-foot stainless steel packed column containing 10% silica gel (SC-30) and employing temperature programming from 60° C. at 20 per minute. The following results were obtained for the Recycle Stream:

Table III

REPRESENTATIVE COMPOSITION OF RECYCLE STREAMS[4]

| Compounds[5] | Fraction 1 Distillation (wt.%) | Distillation Bottoms (wt.%) | Autoclave Residuals (wt.%) |
|---|---|---|---|
| CS$_2$ | 0.4 | — | — |
| PCl$_3$ | 60.4 | — | 3.0 |
| POCl$_3$ | 0.2 | — | — |
| PSCl$_3$ | 29.5 | — | — |
| MPTD | 0.4 | — | — |
| EPTD | 9.2 | 5.1 | 36.4 |
| DEPT | — | 25.7 | 3.9 |
| BIS | — | 20.3 | 3.3 |
| Others | — | 5.7 | — |
| Residues | — | 43.2 | 52.1 |

[4]The data from Example 14 is presented as a representative sample. A dash indicates no product detected.
[5]The following nomenclature was used:
MPTD-CH$_3$P(S)Cl$_2$
EPTD-C$_2$H$_5$P(S)Cl$_2$
DEPT-(C$_2$H$_5$)$_2$P(S)Cl
BIS-Cl$_2$P(S)C$_2$H$_4$P(S)Cl$_2$ The conversion and yield rates based on various starting materials were also computed. The material balance for the reaction is also reported. Inability to account for 100% of the reactants can be ascribed in large part to losses during material handling.

The results are reported in Table IV below:

TABLE IV

A FOURTEEN RUN RECYCLE SERIES FOR EPTD SYNTHESIS YIELD AND CONVERSION DATA

| Example or Run Number | Material Balance | % Conversion[6] C$_2$H$_6$ | % Conversion[6] PSCl$_3$ | % Yield EPTD | % Yield HCl[7] |
|---|---|---|---|---|---|
| 1 | 100% | 57.5 | 95.8 | 53.4 | 85.0 |

TABLE IV-continued
A FOURTEEN RUN RECYCLE SERIES FOR EPTD SYNTHESIS YIELD AND CONVERSION DATA

| Example or Run Number | Material Balance | % Conversion[6] $C_2H_6$ | % Conversion[6] $PSCl_3$ | % Yield EPTD | % Yield HCl[7] |
|---|---|---|---|---|---|
| 2 | 97% | 70.0 | 91.2 | 69.9 | 83.0 |
| 3 | 97% | 66.0 | — | 82.1 | 82.0 |
| 4 | 95.5% | 69.2 | 94.9 | 84.6 | 84.5 |
| 5 | 97.0% | 67.8 | 93.9 | 84.3 | 82.5 |
| 6 | 94.3% | 68.4 | 93.7 | 83.0 | 84.5 |
| 7 | 95.0% | 68.9 | 93.1 | 85.5 | 81.3 |
| 8 | 97.5% | 70.5 | 93.6 | 91.1 | 79.5 |
| 9 | 97.3% | 71.5 | 94.3 | 92.2 | 87.0 |
| 10 | 99.7% | 73.0 | 92.8 | 93.0 | 75.5 |
| 11 | 95.0% | 72.0 | 91.9 | 91.5 | 76.0 |
| 12 | 93.0% | 70.5 | — | 89.9 | 79.0 |
| 13 | 95.6% | 71.5 | — | 89.0 | 77.0 |
| 14 | 96.3% | 70.5 | 94.5 | 92.0 | 73.5 |

[6]Yield and conversion based on fresh, charged $PSCl_3$.
[7]Yield based on fresh, charged $PSCl_3$ assuming 1 mole of HCl per mole of $PSCl_3$.

The residuals left after the reaction were analyzed. Of the total accumulated residuals of 62.6 grams, 29.6 grams were distillation bottoms and 33.0 grams autoclave residuals. The distillation bottoms contained $PCl_3$, EPTD, DEPT, $Cl_2P(S)C_2H_4P(S)Cl_2$, and a minor amount (less than 2% of other materials.

The solid residue in the autoclave upon washing with $P(S)Cl_3$ yielded 7 grams of a char lining, 8 grams of $P(S)Cl_3$ soluble tars and 15 grams of insoluble tars. The soluble residues of the autoclave washing contained mainly EPTD.

DISCUSSION

As it can be seen from the results of Table II, the yield of EPTD using no recycle was 53.4% based on charged $P(S)Cl_3$ (Example 1) using a 25% excess of ethane. Example 1 of U.S. Pat. No. 3,790,629 reports a yield of 70% using 150% excess ethane. Of the liquid poured from the autoclave in U.S. Pat. No. 3,790,629 (61 grams), 84% was product and 16% was by-product. Of the liquid poured from the autoclave (approximately 81 grams) in Example 1 of the present invention, 61.9% was product and 38.1% was by-product. The use of a small excess of ethane increases by-product formation and decreases yield.

In Example 2, the autoclave residuals (8 grams or 6.5% of original charge) along with the residuals from product separation (30.7 grams or about 25% of the original charge) were recycled in the next charge. Yield increased to 69.9% based on the $P(S)Cl_3$ of the fresh charge. The additional by-products generated by Example 2 accounted for 20.6 grams of the total accumulated recycle stream of 59.3 grams over the 38.7 grams of Recycle generated in Example 1.

In the 12 succeeding examples, the same procedure was followed. Yields increased to a median of about 91% by Example 8 with yields of over 80% achieved by Example 3. The recycle stream (autoclave residuals and residuals from product separation) reached a steady state at Example 7. The total recycle stream did not accumulate further amounts in succession charges after Example 7. It must be understood that some material is lost in handling as evidenced by the data given on material balance. This accounts for a portion of the charge which in theory should remain after each reaction due to yields of less than 100%. The quantity of low boiling by-products (Fraction 1) did not vary significantly after Example 4.

An inspection of the data indicates that maximum yields are realized as the residuals reach a steady state of concentration. Yields of over 90% can be achieved without using a large excess of ethane as required in U.S. Pat. No. 3,790,629.

The ethane conversion remained constant from Example 4 at about 70%.

The $P(S)Cl_3$ conversion was about 93% per experiment. For the fourteen examples, a total of 1400 grams of $P(S)Cl_3$ was charged. Only 5.5 grams remained unreacted for an accumulative total conversion of 99.6%.

EXAMPLES 15-20

The procedure of Example 1 was repeated with the exception that a distillation column was not used. 84.5 grams (0.5 moles) $P(S)Cl_3$ and 17.8 grams (0.6 moles) ethane were charged for each successive run. In Example 15, 20.5 milliliters of a 19N NaOH solution was used to neutralize the scrubbing water. This corresponds to 0.39 moles of acid. The wet test meter recorded 4.2 liters of gas of 25° C. which corresponds to 0.171 moles of gas which is mostly unreacted ethane. 126.8 grams of crude liquid product was obtained and analyzed.

The results of this and the succeeding examples are reported in Table V below:

TABLE V
EPTD SYNTHESIS FROM $P(S)Cl_3$ WITH RECYCLING BY-PRODUCTS

| Example No. | Recycle No. | EPTD[8] Yield (% on $PSCl_3$) | HCl[9] Yield (% on $PSCl_3$) | $PSCl_3$[8] Conversion (%) | Ethane Conversion (%) |
|---|---|---|---|---|---|
| 15 | initial | 50.4 | 84.4 | 96.4 | 61.0 |
| 16 | 1 | 66.1 | 75.0 | 92.7 | 60.8 |
| 17 | 2 | 79.6 | 89.4 | 93.2 | 70.4 |
| 18 | 3 | 85.5 | 78.0 | 92.9 | 70.8 |
| 19 | 4 | 86.5 | 74.8 | 94.5 | 70.0 |
| 20 | 5 | 85.5 | 66.7 | 94.1 | 68.5 |

[8]Yield and conversion based on fresh, charged $PSCl_3$. The amount of EPTD is calculated from the gc analysis of the product cut.
[9]Yield based on fresh, charged $PSCl_3$ assuming 1 mole of HCl per mole of $PSCl_3$.

The cumulative results of product and by-product are reported in Table VI below:

TABLE VI
CUMULATIVE RESULTS OF EXAMPLES 15-20

Total Charge
507.5 g. (3.00 mole) $PSCl_3$
112.2 g. (3.74 mole) Ethane

Total Output

| Compound | Weight (g. mole) | % Yield (on $PSCl_3$) |
|---|---|---|
| EPTD[1] | 385.4 (2.30) | 77.0% or 91.5% on consumed ethane |
| HCl[2] | 94.5 (2.60) | 86.5% |
| $C_2H_6$ | 36.7 (1.22) | 66.5% conversion |
| Solid Residue | 18.7 | 4.8 wt. % on EPTD |
| $PCl_3$ | 13.4 (0.097) | 3.2% |
| $Et_2PSCl$ | 7.6 (0.048) | 1.6% |
| $((CH_2P(S)Cl_2))_2$ | 7.1 (0.024) | 1.6% |
| $PSCl_3$ | 5.2 | 99% conversion |
| 2-Cpds[3] | 1.7 | |
| $CS_2$ | 1.6 | |
| $MeP(S)Cl_2$ | 0.9 | 0.23 wt. % on EPTD |
| $EtSP(S)Cl_2$ | 0.6 | |
| $POCl_3$ | 0.4 | |
| Total Production | 573.8 g. | Mass balance of 92.6% |

[1]Includes 6.6 g. of EPTD obtained from washing the autoclave with $CHCl_3$ after the last (5th recycle) run.
[2]This HCl includes a correctiion factor of 2.0 g. per run. About 2.0 g. of HCl remained dissolved in the liquid product until distillation and was therefore not measured by venting at room temperature.
[3]These two compounds are $Cl_2PCH_2CH_2P(S)(Cl)C_2H_5$ and $C_2H_5SP(S)(Cl)C_2H_5$.

The composition of the low boiling fraction (fraction I), the product fraction (fraction II), and the volatile components in the residue remaining after Example 20

(Residue - Fraction III) were determined. The data is reported in Table VII, VIII and IX below:

TABLE VII
COMPOSITION OF FRACTION I (LOW BOILING)

| Example No. | 15 | 16 | 17 | 18 | 19 | 20 |
|---|---|---|---|---|---|---|
| Weight of Fraction I(g) | 14.5 | 20.7 | 22.2 | 21.2 | 17.4 | 19.2 |
| $PCl_3$(g./wt.%) | 8.1 / 56% | 10.7 / 52% | 12.1 / 54% | 11.5 / 54% | 9.7 / 56% | 9.8 / 51% |
| EPTD(g./wt.%) | 3.1 / 21% | 4.2 / 20% | 5.0 / 23% | 4.3 / 20% | 3.2 / 18% | 4.0 / 21% |
| $PSCl_3$(g./wt.%) | 2.1 / 14% | 4.8 / 23% | 4.5 / 20% | 4.3 / 20% | 2.9 / 17% | 3.4 / 18% |
| $CS_2$(g./wt.%) | 0.60 / 4.1% | 0.70 / 3.4% | 0.30 / 1.3% | 0.05 / — | 0.03 / — | 1.6 / 8.0% |
| $MeP(S)Cl_2$(g./wt.%) | 0.14 / 1.0% | 0.05 / 0.2% | 0.15 / 0.7% | 0.13 / 0.6% | 0.12 / 0.7% | 0.08 / 0.4% |
| $POCl_3$(g./wt.%) | 0.20 / 1.4% | 0.20 / 1.0% | 0.20 / 0.9% | 1.7 / 8.0% | 1.4 / 8.1% | 0.33 / 1.7% |

TABLE VIII
COMPOSITION OF FRACTION II (PRODUCT FRACTION)

| Example No. | 15 | 16 | 17 | 18 | 19 | 20 |
|---|---|---|---|---|---|---|
| Recycle No. | initial | 1 | 2 | 3 | 4 | 5 |
| Weight of Fraction II (g.) | 42.2 | 55.5 | 67.0 | 72.4 | 74.0 | 72.2 |
| EPTD(g./wt.%) | 41.0 / 97.5% | 53.8 / 97.2% | 64.9 / 97.0% | 69.6 / 96.2% | 70.7 / 95.5% | 69.6 / 96.5% |
| $PSCl_3$(g./wt.%) | 0.46 / 1.1% | 1.1 / 2.0% | 1.1 / 1.6% | 1.5 / 2.1% | 1.5 / 2.0% | 1.5 / 2.1% |
| $Et_2P(S)Cl$(g./wt.%) | 0.46 / 1.1% | 0.34 / 0.6% | 0.68 / 1.0% | 0.75 / 1.0% | 1.0 / 1.4% | 0.80 / 1.1% |
| $MeP(S)Cl_2$(g./wt.%) | 0.05 / 0.12% | 0.07 / 0.12% | 0.10 / 0.15% | 0.25 / 0.34% | 0.21 / 0.28% | 0.19 / 0.26% |
| $PCl_3$(g./wt.%) | 0.06 / 0.1% | 0.04 / — | 0.15 / 0.2% | 0.18 / 0.2% | 0.52 / 0.7% | 0.12 / 0.2% |
| $EtSP(S)Cl_2$(g./wt.%) | 0.11 / 0.3% | 0.07 / 0.1% | 0.09 / 0.1% | 0.10 / 0.1% | 0.10 / 0.1% | 0.06 / 0.1% |

TABLE IX
COMPOSITION OF FRACTION III (FINAL RESIDUE)

| Example No. | 15 | 16 | 17 | 18 | 19 | 20 |
|---|---|---|---|---|---|---|
| Recycle No. | initial | 1 | 2 | 3 | 4 | 5 |
| Weight of volatile fraction and residue (g.) | 11.3 | 21.6 | 23.8 | 28.5 | 26.1 | 25.7 |
| Weight of Residue(g.) | 4.8[1] | | | Not separated from Fraction II until last run. | | |

% COMPOSITION OF VOLATILE COMPONENTS

| | | | | | | |
|---|---|---|---|---|---|---|
| BIS | 30% | 62% | 54% | 46% | 44% | 39% / 6.6g. |
| EPTD | 33% | 18% | 15% | 19% | 19% | 31% / 5.3g. |
| $Et_2P(S)Cl$ | 24% | 10% | 15% | 16% | 18% | 18% / 3.1 g. |
| BIS-Et[2] | 2.7% | 1.2% | 10% | 11% | 9.9% | 4.1% / 0.7g. |
| Others[3] | 10% | 8.7% | 3.6% | 7.6% | 7.6% | 8.2% / 1.4g. |

[1] Estimated from a run with recycling.
[2] BIS-Et—$Cl_2(S)PCH_2CH_2P(S)$ $(Cl)C_2H_5$.
[3] Others include $MeP(S)$ (Cl)Et, $EtSP(S)Cl_2$, $EtSP(S)ClEt$, $Cl_2(S)PCH_2P(S)Cl_2$ and two unknown compounds.

DISCUSSION

As it can be seen from the data reported above, results similar to those reported in Examples 1-14 were obtained.

The accumulated results of the by-products of Examples 15-20 are shown in Table X below:

TABLE X

| Major By-Products | Yield for a Single[10] Run (2184-35) | Yield for Six Recycle Runs |
|---|---|---|
| PCl3 | 9.3g. (13.5%) | 13.4g. (3.2%) |
| $MeP(S)Cl_2$ | 0.4g. (0.83 wt. %) on EPTD | 0.9g. (0.23 wt. %) on EPTD |
| $Et_2P(S)Cl$ | 1.9g. (2.5%) | 7.6g. (1.6%) |
| BIS | 1.7g. (2.2%) | 7.1g. (1.6%) |
| Residue | 5.3g. (11 wt. %) on EPTD | 18.7g. (4.8 wt.) on EPTD |

[10] Unless specified otherwise, yields are based on the total charge of $PSCl_3$.

As it can be seen from the results, the yield of $PCl_3$, based on $PSCl_3$, decreases from 13.5% for a single run to 3.2% for the recycle runs. The yield of methylphosphonothioic dichloride based on weight of EPTD decreased from 0.83 wt.% to 0.23 wt.%. The yield of diethylphosphonothioic chloride on $PSCl_3$ decreased only slightly with recycling, from 2.5% to 1.6%. The yield of ethylene bisphosphonothioic dichloride (BIS) based on $PSCl_3$ decreased slightly with recycling, from 2.2% to 1.6%. The weight yield of residue based on weight of EPTD decreased from 11 wt.% for a single run to 4.8 wt.% for the six recycle runs. The 18.7g. of residue includes 8.7g. of distillation residue, 5.5g. washed from the autoclave with $CHCl_3$ and 4.5g. washed from the autoclave with a hot 25% caustic solution.

As it can be seen from the preceding examples, EPTD can be effectively prepared in high yields of about 90% by the autoclave reaction of ethane and $P(S)Cl_3$ using substantially stoichiometric quantities of ethane. By-product amounts can be stabilized unexpectedly by recycling all distillation by-products and using the autoclave residues for succeeding reactions.

EXAMPLES 21-25

Insitu formation of $P(S)Cl_3$

In a 300 milliliter stainless steel autoclave was charged for each run 75.6 grams (0.55 moles) of $PCl_3$, 17.6 grams (0.55 moles) of rolled sulfur and 3 grams of carbon (Nuchar C-190). The carbon was added only to the first run. The autoclave was cooled and 18 grams (0.6 moles) of ethane was added to each run. All runs were heated at 325°-335° C. for five hours. After cooling, the autoclave was vented and the HCl collected in a caustic trap. The crude product was distilled at 12 millimeters Hg pressure to a vapor temperature of 50°-55° C. All material collected under these conditions was considered as a low boiling fraction which was recycled to successive runs. The main fraction was distilled at 0.1 millimeters of Hg using a heated water bath. The still bottoms were suspended in fresh $PCl_3$ and recycled. The results are reported in Table XI below:

tion of the reaction, the autoclave was cooled and vented. Unreacted ethyl chloride was collected and the amount determined by a wet meter. The crude product was distilled to remove the low boiling fraction and the product $(C_2H_5P(S)Cl_2)$ fraction. The results are reported in Table XIII below:

TABLE XI
EPTD RECYCLE STUDY (IN SITU FORMATION OF P(S)Cl₃)

| Example | Cycle No. | Grams | Ventloss grams | HCl moles | Distillation (grams) | | | Products (moles)* | | | % Yield |
| | | | | | Low Boiling Fraction | Product Fraction | Residue | PSCl₃ | EPTD | Et₂PSCl | |
|---|---|---|---|---|---|---|---|---|---|---|---|
| 21 | 1 | 114 | 22 | .42 | 11.5 | 52.8 | 15.3 | .008 | .310 | .005 | 56% |
| 22 | 2 | 138 | 27 | .42 | 17.7 | 60.1 | 27.7 | .008 | .358 | .002 | 65% |
| 23 | 3 | 156 | 21 | .43 | 7.0 | 75.7 | 34.3 | .021 | .440 | 001 | 80% |
| 24 | 4 | 157 | 20 | .44 | 6.5 | 79.6 | 37.0 | .023 | .458 | .005 | 83% |
| 25 | 5 | 155 | 24 | .43 | 2.8 | 83.8 | 39.0 | .012 | .490 | .013 | 89% |

(Final analysis low boiling fraction: 36% PCl₃; 11.3% EPTD)
*Product (moles) = product (grams) × assay %/100 ÷ MW After the last run, the autoclave was washed with chloroform and the solution was evaporated. Approximately 5 grams remained in the autoclave. The 39 grams of residue obtained after evaporation of the chloroform was extracted with chloroform. It was 44.4% insoluble in chloroform. The chloroform soluble fraction was analyzed by $^{31}$P-nmr and appears to be 55% $Cl_2P(S)CH_2CH_2P(S)Cl_2$, 5% EPTD, 5% DEPT, and six unknown components.

By this reaction, it can be seen that $PX_3$ and S can be effectively used to prepare $P(S)Cl_3$ in situ in a recycle reaction.

EXAMPLES 26–29

Reaction $\phi H + P(S)Cl_3 \rightarrow \phi P(S)Cl_2$

The procedure of Example 21 was repeated using benzene and thiophosphoryl chloride. The reaction was conducted at 320° C. for ten hours not including heat up and cool down times. By-products residue continued to accumulate even though the amount of reactants was reduced. Recycling achieved an average yield increase of 18%. The results are reported in Table XII below:

TABLE XII
REACTION $\phi OH/P(S)Cl_3$

| Example | Recycle No. | Charge (moles) | Product (moles) $\phi P(S)Cl_2$ | Yield | Grams Residue | Grams Recycle |
|---|---|---|---|---|---|---|
| 26 | 1 | 0.6 φH<br>0.5 P(S)Cl₃ | 0.265 | 53% | 24 | 0 |
| 27 | 2 | 0.49 φH<br>0.48 P(S)Cl₃ | 0.343 | 71% | 34 | 24 |
| 28 | 3 | 0.32 φH<br>0.40 P(S)Cl₃ | 0.305 | 76% | 45 | 35 |
| 29 | 4 | 0.37 φH<br>0.378 P(S)Cl₃ | 0.256 | 68% | 35 | 22.5 |

EXAMPLES 30–40

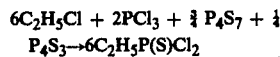

$P_4S_3 \rightarrow 6C_2H_5P(S)Cl_2$

In a 300 milliliter stainless steel autoclave equipped with a 3-way valve and a 2000 psi blow-out disc were placed 60.3 grams (0.935 moles) of ethyl chloride, 34.3 grams (0.25 moles) of $PCl_3$, 6.9 grams (0.031 moles) of $P_4S_3$, and 32.6 grams (0.094 moles) of $P_4S_7$. The autoclave was heated to 325° C. for six hours. Upon comple-

TABLE XIII

| Ex. | Recycle No. | EPTD (grams) | % Yield EPTD | Distillation Bottoms | Autoclave Residuals | Total Residuals |
|---|---|---|---|---|---|---|
| 30 | 1 | 66 | 54 | 23 | 3 | 26 |
| 31 | 2 | 78.4 | 64 | 47 | 3 | 50 |
| 32 | 3 | 88.2 | 72 | 58 | 5 | 63 |
| 33 | 4 | 94.8 | 78 | 74 | 5 | 79 |
| 34 | 5 | 98 | 80 | 86 | 8 | 94 |
| 35 | 6 | 101 | 83 | 86 | 20 | 106 |
| 36 | 7 | 102 | 84 | 101 | 13 | 114 |
| 37 | 8 | 101.5 | 83 | 101 | 22 | 123 |
| 38 | 9 | 103.7 | 85 | 103 | 26 | 129 |
| 39 | 10 | 95 | 78** | 100 | 29 | 129 |
| 40 | 11 | 103 | 84 | 105 | 32 | 137 |

**Material loss occurred during venting.

The material balance of the reaction crude was determined as set forth in Table XIV below:

TABLE XIV
MATERIAL BALANCE OF REACTION CRUDE IN GRAMS

| Example | Ref. | Distillation Gases | Low Boiling Fraction | EPTD | DEPT | Distillation Residue |
|---|---|---|---|---|---|---|
| 30 | 1 | 6 | 3.6 | 66 | 10 | 23 |
| 31 | 2 | 8 | 2.9 | 78.4 | 2.3 | 47 |
| 32 | 3 | 10 | 4.0 | 88.2 | 1.5 | 58 |
| 33 | 4 | 8 | 5.0 | 94.8 | 2.3 | 74 |
| 34 | 5 | 8 | 3.0 | 98 | 1.2 | 86 |
| 35 | 6 | 8 | 3.0 | 101 | 1.0 | 86 |
| 36 | 7 | 8 | 3.0 | 102 | 0.8 | 101 |
| 37 | 8 | 5 | 3.0 | 101.5 | 0.5 | 101 |

TABLE XIV-continued
MATERIAL BALANCE OF REACTION CRUDE IN GRAMS

| Example | Ref. | Distillation Gases | Low Boiling Fraction | EPTD | DEPT | Distillation Residue |
|---|---|---|---|---|---|---|
| 38 | 9 | 8 | 3.0 | 95 | 1.2 | 103 |
| 39 | 10 | 5 | 3.0 | 103 | 1.5 | 100 |
| 40 | 11 | 6 | 2.0 | — | — | 105 |
| Totals | | 80 | 2.0 | 1031.6 | 22.3 | 105 |

The total material coming out of the reaction which includes the HCl and ethane vent gases, the autoclave residuals (see Table XIV), the distillation gases, the low boiling fraction DEPT, the distillation residue, and EPTD equals 1403grams. The total reactants put into the autoclave that include $PCl_3$, $P_4S_7$, $P_4S_3$ and ethyl chloride equals 1474 grams or a percent material balance of 95%.

The material balance of material taken from the autoclave was also determined as shown in Table XV below:

TABLE XV
EPTD MATERIAL BALANCE FROM AUTOCLAVE

| Ex. | Recycle No. | Autoclave[2] Grams In | Autoclave[2] Grams Out | Residuals | HC[1] grams | Ethane Gas grams | Material Balance |
|---|---|---|---|---|---|---|---|
| 30 | 1 | 134 | 113 | 3 | 6 | 6 | 96% |
| 31 | 2 | 157 | 141 | 3 | 10 | 3 | 100% |
| 32 | 3 | 183 | 161 | 5 | 5 | 5 | 96% |
| 33 | 4 | 201 | 185 | 5 | 4 | 6 | 99% |
| 34 | 5 | 218 | 196 | 8 | 3 | 11 | 100% |
| 35 | 6 | 231 | 199 | 20 | 5 | 7 | 100% |
| 36 | 7 | 243 | 216 | 13 | 3 | 7 | 98% |
| 37 | 8 | 250 | 212 | 22 | 4 | 6 | 98% |
| 38 | 9 | 259 | 219 | 26 | 4 | 7 | 99% |
| 39 | 10 | 263 | 204 | 29 | 4 | 7 | 93% |
| 40 | 11 | 265 | 220 | 32 | 4 | 7 | 99% |
| | | | | 38 | 52 | 72 | |

[1] Includes the distillation bottoms and autoclave residuals which were accumulated during the previous runs. Before each run the weight of the completely empty autoclave was subtracted from the weight of the loaded autoclave.
[2] Accumulative increase in weight of autoclave residuals, the autoclave was cleaned after the first two runs, so that 6 grams of residuals were lost.

As it can be seen from Table XIII, the yield of EPTD increases from 54% to 83% after the sixth run. The yield remains fairly constant for the remaining runs. The distillation bottoms level off and do not accumulate further. However, the autoclave residues continue to increase contributing to an increase in the overall residue accumulation. Material balance over 11 experiments was 95% indicating only a 5% loss a portion of which is attributable to material handling.

While the preceding examples are directed to EPTD and BPTD, the process is also effective in preparing other phosphonothioic dihalides such as the methyl, propyl, butyl, isobutyl, cyclohexyl, benzyl, tolyl, nonyl and the like.

While the preceding examples illustrate the present invention in connection with the RH and RX type reactions, the invention is also equally applicable to RSaR type reactions.

Further, it can be seen that the invention is not limited to the hydrocarbon/$P(S)Cl_3$ reaction as improved yields can also be obtained in the other autoclave processes mentioned hereinbefore such as the alkyl or aryl halide and $P(S)Cl_3$. Nor is the reaction limited to the chlorine derivatives as bromine can also be used. The thiophosphoryl chloride can be effectively replaced by phosphorus trichloride and sulfur. Any other combination of phosphorus, phosphorus trichloride and phosphorus sulfides which can form phosphorus thiotrichloride per se or provide the same reaction effect in the final product can be used.

The invention is defined in the claims which follow.
What is claimed is:

1. In a method for preparing compounds of the formula:

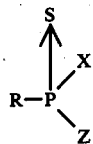

wherein R is a $C_1$ to $C_{20}$ alkyl radical, cycloalkyl of 5-6 carbon atoms in the ring and the $C_1$-$C_4$ alkyl substituted derivative thereof, an aralkyl radical of up to two fused rings, the alkyl portion having from 1 to 20 carbon atoms, an aryl radical of up to three fused rings and the $C_1$-$C_4$ alkyl derivatives thereof, and biphenyl and the $C_1$-$C_4$ alkyl derivatives thereof, X is a halogen of chlorine or bromine, and Z is either R or X, by the reaction of a phosphorus halide source under autogenous pressure in a reaction zone capable of withstanding elevated pressure at a temperature ranging from about 175° to about 450° C., the improvement which comprises recycling in successive runs a by-product of the reaction remaining after separation of the RP(S)XZ product fraction selected from the group consisting of:
(a) a by-product fraction having a boiling point lower than the product fraction;
(b) a by-product fraction having a boiling point higher than the product fraction when said hydrocarbon source is a member selected from the group consisting of RX and $RS_aR$;
(c) a by-product fraction having a boiling point higher than a product fraction having the formula RP(S)XZ wherein Z is R;
(d) XZP(S)RP(S)XZ;
(e) liquid residue;
(f) solid residue;
(g) mixture thereof; and
(h) mixtures thereof with a member selected from the group consisting of $R_2P(S)X$ and the by-product fraction having a boiling point higher than the product fraction where said hydrocarbon source is RH wherein R and X are as defined hereinbefore.

2. The method as recited in claim 1 wherein said by-product fraction which is recycled is a mixture of said fraction boiling lower and higher than the product fraction, the liquid residues and the solid residues.

3. The method as recited in claim 1 wherein Z is halogen.

4. The method as recited in claim 1 wherein Z and X are chlorine.

5. The method as recited in claim 1 wherein R is $C_1$-$C_6$ alkyl.

6. The method as recited in claim 1 wherein said reaction is conducted at a temperature within the range of from about 200° C. to about 400° C.

7. The method as recited in claim 1 wherein said phosphorus halide source is thiphosphoryl chloride.

8. The method as recited in claim 7 wherein said thiophosphoryl chloride is formed in situ from phosphorus trichloride and sulfur.

9. The method as recited in claim 1 wherein said hydrocarbon source is an RH compound.

10. The method as recited in claim 9 wherein said hydrocarbon is ethane.

11. The method as recited in claim 1 wherein said hydrocarbon source is an RX compound.

12. The method as recited in claim 11 wherein the RX compound is a halogenated $C_1$-$C_6$ alkyl.

13. The method as recited in claim 12 wherein said alkyl is ethyl.

14. The method as recited in claim 1 wherein R is a $C_1$-$C_6$ alkyl, X is chlorine, Z is X, the phosphorus halide source and the sulfur source is thiophosphoryl halide, and the hydrocarbon source is ethane.

15. The method as recited in claim 14 wherein said by-product fraction which is recycled is a mixture of said fractions boiling lower and higher than the product fraction, the liquid residues and the solid residues.

* * * * *

UNITED STATES PATENT AND TRADEMARK OFFICE
CERTIFICATE OF CORRECTION

PATENT NO. : 4,133,830
DATED : January 9, 1979
INVENTOR(S) : Eugene H. Uhing and Arthur D. F. Toy It is certified that error appears in the above-identified patent and that said Letters Patent are hereby corrected as shown below:

Column 2, line 56, "production" should be -- product --.

Column 5, line 1, "dodecyl, chloride" should be -- dodecyl chloride --.

Column 9, line 40, "Anthracine" should be -- Anthracene --.

Column 17, Table XI (in the footnotes) after "$PSCl_3$;" please insert -- 52.3% $PSCl_3$ --.

Column 19, line 22, Table XV, "$HC^1$" should be -- HCl --.

Column 20, Claim 7, line 58, "thiphosphoryl" should be -- thiophosphoryl --.

Signed and Sealed this

Fifth Day of June 1979

[SEAL]

Attest:

RUTH C. MASON
Attesting Officer

DONALD W. BANNER
Commissioner of Patents and Trademarks